US011266530B2

(12) United States Patent
Hendrix

(10) Patent No.: US 11,266,530 B2
(45) Date of Patent: Mar. 8, 2022

(54) ROUTE GUIDANCE AND OBSTACLE AVOIDANCE SYSTEM

(71) Applicant: Jennifer Hendrix, Waxahachie, TX (US)

(72) Inventor: Jennifer Hendrix, Waxahachie, TX (US)

(*) Notice: Subject to any disclaimer, the term of this patent is extended or adjusted under 35 U.S.C. 154(b) by 0 days.

(21) Appl. No.: 16/361,870

(22) Filed: Mar. 22, 2019

(65) Prior Publication Data

US 2019/0290492 A1    Sep. 26, 2019

Related U.S. Application Data

(60) Provisional application No. 62/646,708, filed on Mar. 22, 2018.

(51) Int. Cl.
| | | |
|---|---|---|
| *A61F 9/08* | (2006.01) | |
| *G06T 7/70* | (2017.01) | |
| *G06K 9/00* | (2006.01) | |
| *G06F 3/01* | (2006.01) | |

(52) U.S. Cl.
CPC .......... *A61F 9/08* (2013.01); *G06F 3/012* (2013.01); *G06K 9/00671* (2013.01); *G06T 7/70* (2017.01)

(58) Field of Classification Search
CPC ......... A61F 9/08; G06T 7/70; G06K 9/00671; G06K 9/00771; G06F 3/012
See application file for complete search history.

(56) References Cited

U.S. PATENT DOCUMENTS

| | | | | |
|---|---|---|---|---|
| 6,757,068 | B2* | 6/2004 | Foxlin | G02B 27/017 |
| | | | | 356/139.03 |
| 2005/0189503 | A1* | 9/2005 | Jamieson | G01N 21/251 |
| | | | | 250/559.4 |
| 2015/0324646 | A1* | 11/2015 | Kimia | G06T 7/80 |
| | | | | 348/62 |
| 2018/0109900 | A1* | 4/2018 | Lyren | H04S 7/304 |
| 2018/0181201 | A1* | 6/2018 | Grant | G06F 3/016 |
| 2018/0189567 | A1* | 7/2018 | Maheriya | G06K 9/00214 |

OTHER PUBLICATIONS

Ribeiro (Auditory Augmented Reality: Object Sonification for the Visually Impaired—2012 IEEE 14th International Workshop on Multimedia Signal Processing (MMSP) Date Added to IEEE Xplore: Nov. 12, 2012; DOI: 10.1109/MMSP.2012.6343462 (Year: 2012).*
Office Action in related CA application No. 3,037,657, dated Apr. 14, 2020, 5 pages.

* cited by examiner

*Primary Examiner* — Nasim N Nirjhar
(74) *Attorney, Agent, or Firm* — Law Office of Jeff Williams PLLC; J. Oliver Williams

(57) ABSTRACT

A route guidance and obstacle avoidance system for the visually impaired includes a main body assembly worn around the body of the user and a headset assembly worn around the head of the user. The system incorporates obstacle avoidance technology and navigation technology to generate a 3D audio output to a user so as to generate an audible virtual environment reflective of the physical environment of the user. The assemblies include line of sight sensors, a central processing unit, a navigation module, and a camera assembly. Obstacles are detected and classified with a location and distance, and are concurrently processed with real time navigation that is adjusted to instruct not only how to get to a location but also how to avoid obstacles.

20 Claims, 5 Drawing Sheets

ROUTE GUIDANCE AND OBSTACLE AVOIDANCE SYSTEM

CLAIM OF PRIORITY

This application claims the benefit of U.S. Provisional Application No. 62/646,708, filed 22 Mar. 2018. The information contained therein is hereby incorporated by reference.

BACKGROUND

1. Field of the Invention

The present application relates generally to an electronic navigation and obstacle avoidance system, and in particular to a system designed to provide route guidance and obstacle avoidance feedback audibly to assist visually impaired users navigate without incident.

2. Description of Related Art

The CDC reports that there are more than 285 million people who are blind or visually impaired. More than 7 million people go blind each year in the United States. The World Health Organization (WHO) states that every 5 seconds a person in the world goes blind. Every 1 minute, one of those people is a child. The loss of one's ability to move through the world has the greatest negative impact on human development. Blindness can arise from one of many different causes, such as macular degeneration, accident or injury, diabetes, and so on. Blindness works to severely limit one's ability to be mobile. This lack of mobility inherently results often in the seclusion, depression, and inability of those individuals from engaging in the public environment.

Various methods or devices have been developed to assist blind individuals in navigating and engaging in the public environment. For example, seeing-eye dogs are used to help direct an individual. Although dogs help in terms of general navigation, the dog is unable to provide accurate and detailed navigation to the blind. Additional disadvantages to the use of trained dogs to solve navigation issues is that the training of dogs can be very time consuming and costly. Additionally, distractions may arise which may get in the way of the dog performing despite training.

Another method or device is the elongated stick. The blind individual is tasked with repetitively passing the stick in a sideways motion in front of them to alert them to any obstacles. This stick only provides immediate obstacle detection but provides no additional benefit.

Although great strides have been made in the area of mobility aids for the visually impaired, considerable shortcomings remain in helping them freely navigate through society. Most navigation systems today are designed to provide route guidance with little regard to potential obstacles. Obstacles may be dynamic or static in nature. For example, a map program may provide turn by turn instructions at selected points of interest but does not typically care what happens between such points. These systems deal with a relatively unchanging map to provide routes. Some steps have been taken to design a system that accounts for changes and obstacles on the road. These are incorporated into vehicles to allow the vehicle to adjust speed or stop as obstacles arise. Taken to another level, self-driving cars are contemplated that will autonomously navigate the route on behalf of the user. However, there are large limitations on being able to process and account for obstacles that are dynamic in nature. These cars have an assortment of difficulties in traversing traffic.

On a large scale and in limited situations, these systems may be sufficient. However, traveling or navigating is not always done on standard routes via streets, or outside exposed to the elements. A large amount of our traveling is done inside buildings, amongst ever changing environments from moving people, objects, and hazards. A more portable and adaptable system is needed that will adapt to non-mainstream or high-level routes, provide object detection, and communicate commands to the user to avoid the objects while maintaining the best route to the overall destination. A system such as this is needed especially for visually impaired users to navigate freely in society.

SUMMARY OF THE INVENTION

It is an object of the present application to provide a route guidance and obstacle avoidance system that grants the visually impaired an ability to interact and function within society in a manner that promotes free movement through public spaces. The system addresses the interaction of three areas, namely the user experience, obstacle avoidance, and navigation. The system will sense and compute both dynamic and static obstacles as well as locate the user and calculate navigational information. The information and data are synthesized into a 3D audio output for receipt of the user. This is manifest through binaural, immersive, and spatial audio that transforms the physical world into an audibly defined space. The system updates and monitors in real-time and continuously adapts to the movements and interests of the user.

It is an object of the present application to provide a system that includes a number of wearable electrical components that minimize bulk and avoid limitation to user movements. The system is configured to include a main body assembly to be worn by the user. The main body assembly uses a plurality of electrical components to track and monitor static and dynamic moving objects and process such information for transmission to the user. Additionally, the main body assembly will monitor location and provide navigation. A headset assembly will also be worn by the user and include a plurality of electrical components to receive communication from the main body assembly in the way of binaural audio.

The system will also be equipped with a plurality of sensors that are configured to track line of sight of the user. Such sensors may be located in the main body assembly for determining the orientation or direction of the user; as well as located in the headset assembly to determine the line of sight of the face of the user.

A further object of the present application is to permit a user the ability to adjust the scanning radius for obstacle avoidance.

Another object is to permit the user the ability to apply tags or beacons which are sounds applied to navigational waypoints or destinations; or other people and users. Sound markers may also be designated by the user and applied to objects or obstacles. These markers beacons and tags are useful to a user to distinguish and decipher the environment around him/her.

In one embodiment of the present application the system includes a manual user interface to permit the user the ability to adjust audio markers for particular objects and/or places. This is performed through the use of line of sight technology in combination with the direction of viewing of the user.

It is a further object of the present application that features such as line of sight focus adjustment, route backtracking, route memorization/optimization be available. Ultimately the invention may take many embodiments. In these ways, the present invention overcomes the disadvantages inherent in the prior art.

The more important features have thus been outlined in order that the more detailed description that follows may be better understood and to ensure that the present contribution to the art is appreciated. Additional features will be described hereinafter and will form the subject matter of the claims that follow.

Many objects of the present application will appear from the following description and appended claims, reference being made to the accompanying drawings forming a part of this specification wherein like reference characters designate corresponding parts in the several views.

Before explaining at least one embodiment of the present invention in detail, it is to be understood that the embodiments are not limited in its application to the details of construction and the arrangements of the components set forth in the following description or illustrated in the drawings. The embodiments are capable of being practiced and carried out in various ways. Also it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the various purposes of the present design. It is important, therefore, that the claims be regarded as including such equivalent constructions insofar as they do not depart from the spirit and scope of the present application.

DESCRIPTION OF THE DRAWINGS

The novel features believed characteristic of the application are set forth in the appended claims. However, the application itself, as well as a preferred mode of use, and further objectives and advantages thereof, will best be understood by reference to the following detailed description when read in conjunction with the accompanying drawings, wherein:

Figure 1:
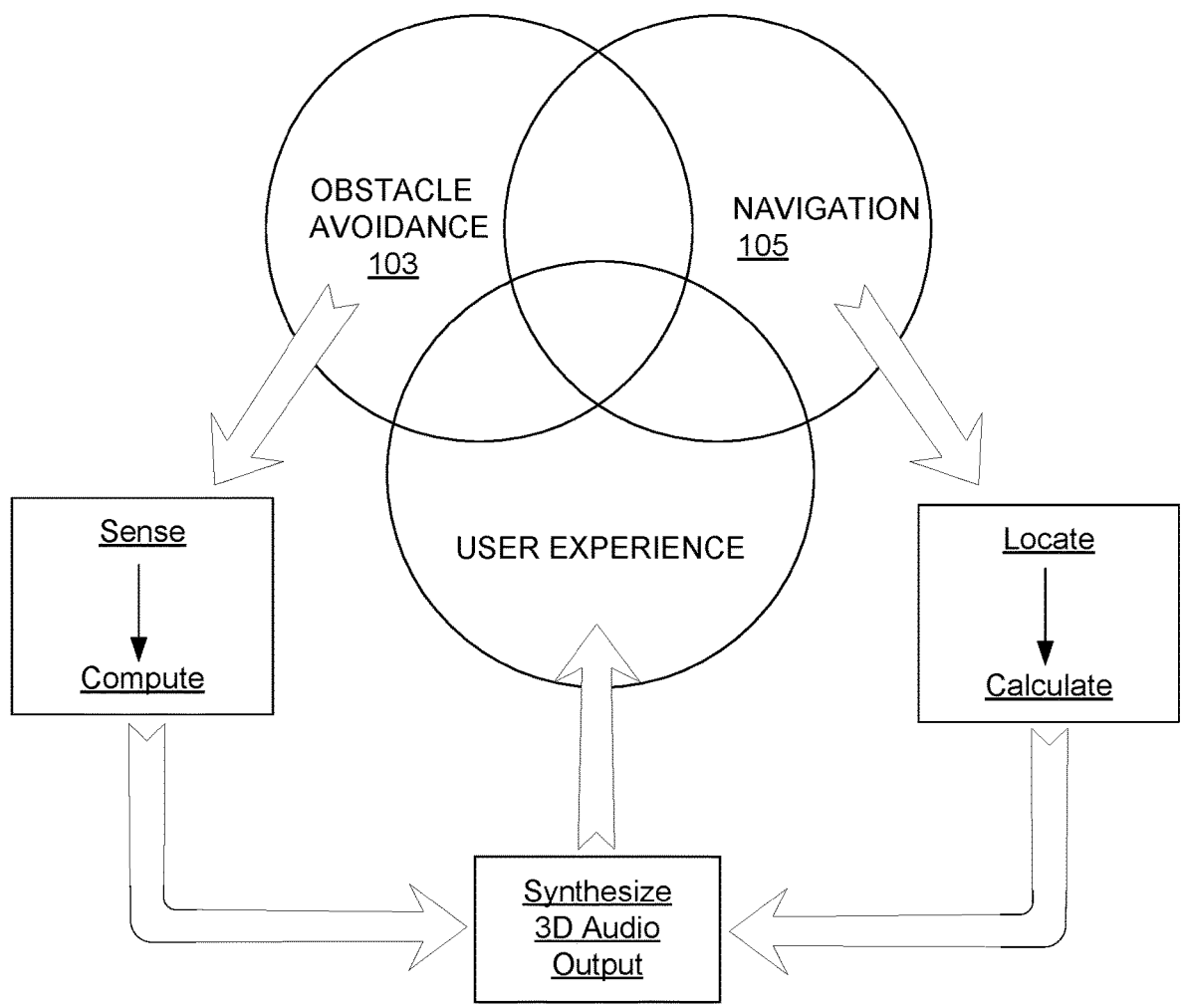
FIG. 1 is a chart of an operative overview of a route guidance and obstacle avoidance system according to an embodiment of the present application.

While the embodiments and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE PREFERRED EMBODIMENT

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the embodiments described herein may be oriented in any desired direction.

The embodiments and method in accordance with the present application overcomes one or more of the above-discussed problems commonly associated with the prior art. In particular, the route guidance and obstacle avoidance system of the present application integrates a plurality of different technologies together to provide an audibly immersive environment representative of the actual environment in which the visually impaired are situated within. The system provides navigation assistance to visually impaired individuals as well as obstacle detection and avoidance capabilities. The system is designed to capture static environmental characteristics and combine that with active detection of both static and dynamic obstructions. These are processed through an algorithm to generate communication information provided to the user as to how best to navigate the environment. The system is configured to provide navigational instruction audibly which may include turn by turn instruction as well as course adjustments to the individual along the route. These and other unique features are discussed below and illustrated in the accompanying drawings.

The embodiments and method will be understood, both as to its structure and operation, from the accompanying drawings, taken in conjunction with the accompanying description. Several embodiments of the assembly may be presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless otherwise described.

Referring now to FIG. 1 in the drawings, a chart showing the operative overview of the route guidance and obstacle avoidance system 101 in accordance with the present application is illustrated. In general, system 101 is configured to be worn by a visually impaired user and may include a main body assembly and a headset assembly. One or more sensors and processors may be included with each to process, monitor, and track movements of the body of the user separate from that of the head of the user. System 101 processes the inputs from each assembly to generate the 3D synthesized audio output which is heard by the user.

System 101 uses assorted technologies (103, 105) in combination with the one or more sensors in each assembly to generate the 3D audio output. A main processor receives data from the one or more sensors associated with obstacle avoidance technology 103 and navigation technology 105 and synthesizes such information in real time to provide a continuously updated audible environment to the user. The audible environment is the 3D audio output which includes real time movement instructions and corrections so as to navigate around detected obstructions along the route, as well as obstacle location and obstacle/landmark identification to permit the user not only movement instructions but a full audible view of what is in the environment as well.

System 101 includes obstacle avoidance technologies 103 and navigation technologies 105. The audible environment created and shared with the user allows them to freely navigate public spaces. Such technologies may include, obstacle detection, head tracking (line of sight—LOS), 3D audio synthesis, virtual reality, navigation and sound design to name a few. System 101 is configured to monitor in real time the environment of the user and convert the data collected into a representative audio environment which can be navigated through. This is accomplished through the combination of technologies 103 and 105 in the main body assembly and the headset assembly.

Obstacle avoidance technologies 103 are configured to sense and compute the location of obstacles. The obstacles may be static or dynamic in movement. A plurality of obstacles may be tracked simultaneously. The act of sensing obstacles are done through one or more wearable sensors. Additionally, a camera may be used to capture visual data around the environment. For example, 3D video for outdoor and structured video for indoor use. The main body assembly may include a line of sight (LOS) sensor to track the directional heading of the user. Data from these sensors are transmitted to one or more processors to compute characteristics of the obstacles, such as identity (i.e. based on shape and/or movement), speed and heading relative to the user, and terrain identification.

Navigation technologies 105 is configured to locate and calculate the location of the user and transmit such data to the one or more processors for synthesizing. Technologies 105 may locate through the use of GPS technology via waypoints. It may also provide the user with landmark information along the route to provide a fuller view of the environment. Warnings that are detected through technology 103 may be synthesized with technology 105 to provide real time warnings that emerge along the route. Additionally, technology 105 can memorize and store particular routes (i.e. commonly traveled or of interest to the user) for use at later times. Likewise, the routes may be backtracked automatically through technology 105 and provided to the user as needed. For example, if a detour was found along a route but not noted through GPS (i.e. sidewalk closed) the user could backtrack along the same route automatically for a short distance to get to another permitted route.

As stated, the system 101 can calculate the position of the user and provide route guidance to the user for a selected destination. Technologies 105 can receive route or map information based on any number of sources, such as GPS for outdoor uses predominantly. Another example is layout data for buildings for indoor use. These may be provided via a terminal at an entrance of the building and automatically synced with system 101 upon entry. The system 101 is configured to alternate between indoor and outdoor navigation seamlessly, or in other words between exterior and interior maps. Location may be done for indoor and outdoor locations and calculations of routes are based upon the waypoints, landmarks, warnings, and obstacles noted above.

The information through technologies 103 and 105 are synced and processed through a central processing unit and synthesized to generate that 3D audio output for the user. This output enhances the user experience and facilitates freedom to move. It is understood that 3D audio output can include binaural audio, immersive audio, directional audio and spatial audio to name a few. Such technologies may be known via different names and have some differences but are useful in trying to bring about the same audible environment to the user. The 3D audio relates to an audible sound that appears to come to the user from a specific distance and direction. The distance and direction is reflected in different ways. For example, the decibel level of the sound can indicate an amount of distance. The sound can then be provided to the user through headphones to provide directional hearing so as to locate the sound relative to the user.

It is understood that system 101 relies upon the creation of an audible environment to represent the actual physical environment of the user. Various sounds may be generated and produced through unit 117. Audio markers related to sounds applied to objects/obstacles. Audio beacons relate to sounds applied to navigational waypoints or destinations. Audio tags related to sound applied to other people/users.

Figure 2:
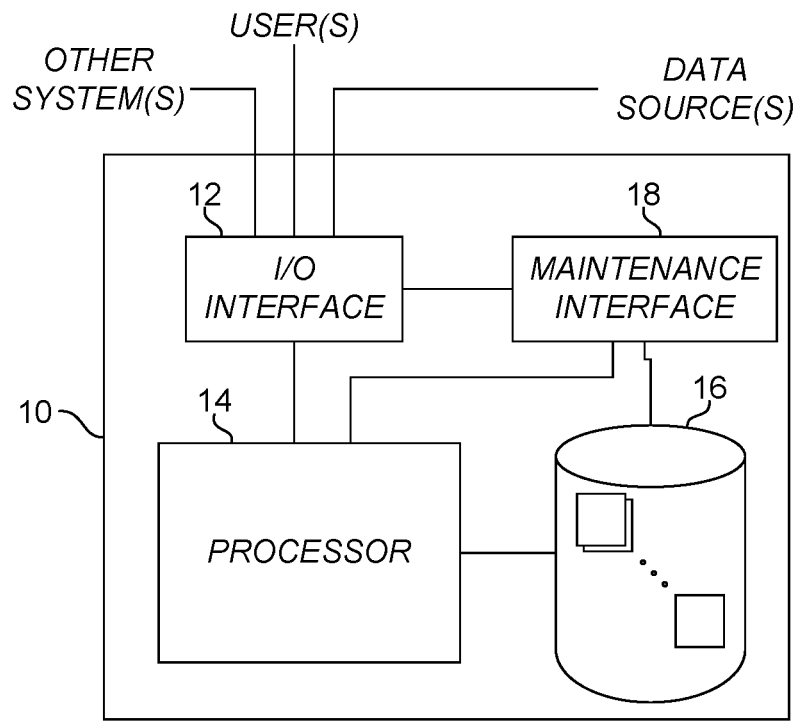
FIG. 2 is an exemplary schematic of an electronic system used in the route guidance and obstacle avoidance system of FIG. 1.

Referring now also to FIG. 2 in the drawings, a schematic of an exemplary electronic computing system for use within system 101 is illustrated. As stated previously, the functions and features of system 101 are such that one or more electronic devices and systems operate in a cooperative manner to produce the 3D audio output. Any of the electronic components or devices in system 101, herein referred to may include a computing system of some type. FIG. 2 illustrates an exemplary set of components used to facilitate the features and functions of system 101.

The computing system 10 includes an input/output (I/O) interface 12, a processor 14, a database 16, and a maintenance interface 18. Alternative embodiments can combine or distribute the input/output (I/O) interface 12, processor 14, database 16, and maintenance interface 18 as desired. Embodiments of the computing system 10 can include one or more computers that include one or more processors and memories configured for performing tasks described herein below. This can include, for example, an electronic computing device (i.e. computer) having a central processing unit (CPU) and non-volatile memory that stores software instructions for instructing the CPU to perform at least some of the tasks described herein. This can also include, for example, two or more computers that are in communication via a computer network, where one or more of the computers includes a CPU and non-volatile memory, and one or more of the computer's non-volatile memory stores software instructions for instructing any of the CPU(s) to perform any of the tasks described herein. Thus, while the exemplary embodiment is described in terms of a discrete machine, it should be appreciated that this description is non-limiting, and that the present description applies equally to numerous other arrangements involving one or more machines performing tasks distributed in any way among the one or more machines. It should also be appreciated that such machines need not be dedicated to performing tasks described herein, but instead can be multi-purpose machines, for example computer workstations and cell phones, that are suitable for also performing other tasks. Furthermore, the computers may use transitory and non-transitory forms of computer-readable media. Non-transitory computer-readable media is to be interpreted to comprise all computer-readable media, with the sole exception of being a transitory, propagating signal.

The I/O interface 12 provides a communication link between external users, systems, and data sources and components of the computing system 10. The I/O interface 12 can be configured for allowing one or more users to input information to the computing system 10 via any known input device. Examples can include a keyboard, mouse, touch screen, microphone, and/or any other desired input device. The I/O interface 12 can be configured for allowing one or more users to receive information output from the computing system 10 via any known output device. Examples can include a display monitor, a printer, a speaker, and/or any other desired output device. The I/O interface 12 can be configured for allowing other systems to communicate with the computing system 10. For example, the I/O interface 12 can allow one or more remote computer(s) to access information, input information, and/or remotely instruct the computing system 10 to perform one or more of the tasks described herein. The I/O interface 12 can be configured for allowing communication with one or more remote data sources. For example, the I/O interface 12 can allow one or more remote data source(s) to access information, input information, and/or remotely instruct the computing system 10 to perform one or more of the tasks described herein.

The database 16 provides persistent data storage for computing system 10. While the term "database" is primarily used, a memory or other suitable data storage arrangement may provide the functionality of the database 16. In alternative embodiments, the database 16 can be integral to or separate from the computing system 10 and can operate on one or more computers. The database 16 preferably provides non-volatile data storage for any information suitable to support the operation of the computing system 10, including various types of data discussed below.

The maintenance interface 18 is configured to allow users to maintain desired operation of the computing system 10. In some embodiments, the maintenance interface 18 can be configured to allow for reviewing and/or revising the data stored in the database 16 and/or performing any suitable administrative tasks commonly associated with database management. This can include, for example, updating database management software, revising security settings, linking multiple devices, and/or performing data backup operations. In some embodiments, the maintenance interface 18 can be configured to allow for maintenance of the processor 14 and/or the I/O interface 12. This can include, for example, software updates and/or administrative tasks such as security management and/or adjustment of certain tolerance settings.

The processor 14 is configured receive communication data from one or more sources, such as technologies 103 and 105, and process that data according to one or more user parameters. Examples of parameters could be limitations, warnings, time related functions, spatial restrictions such as location limitations, and so forth. The processor 14 can include various combinations of one or more computing systems, memories, and software components to accomplish these tasks and functions. The communication data from technologies 103 and 105 are synthesized and processed to generate the 3D audio output for the user to listen to.

Figure 3:
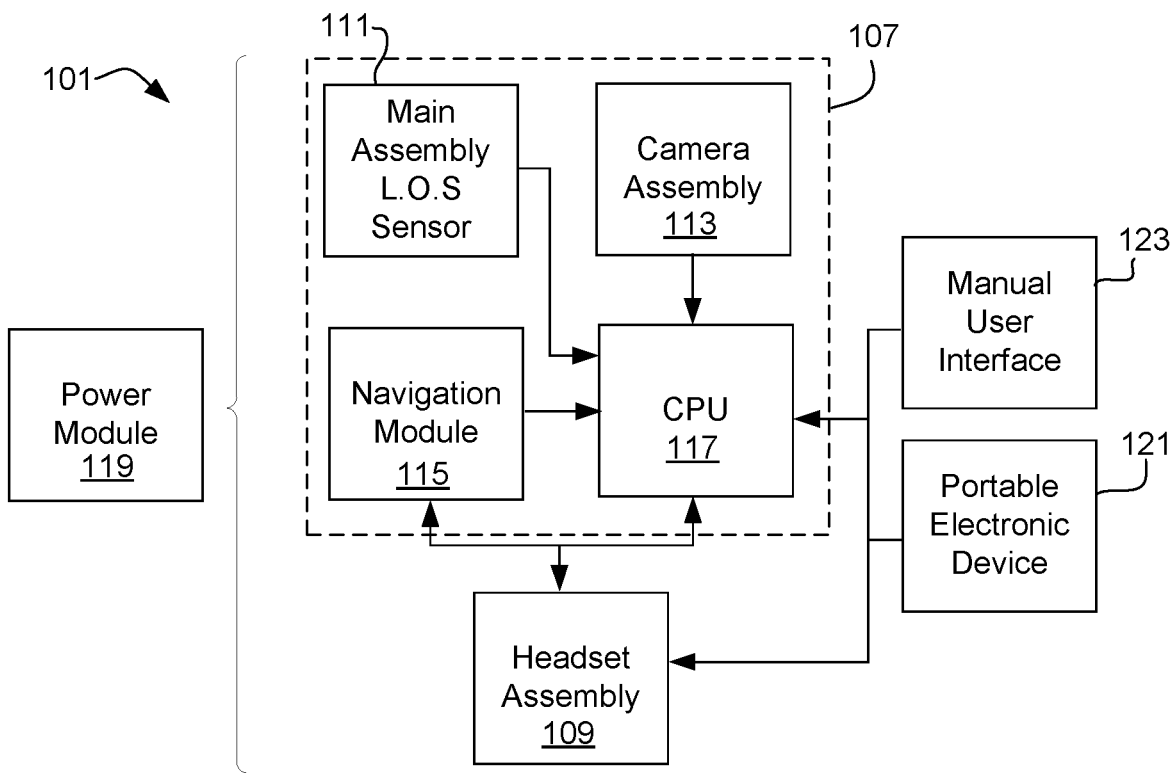
FIG. 3 is a diagram of the route guidance and obstacle avoidance system according to an embodiment of the present application.

Referring now also to FIG. 3 in the drawings, a diagram of system 101 is illustrated. The embodiments and method of the present application are illustrated in the associated drawings. System 101 includes a main body assembly 107 including a line of sight sensor 111 and a central processing unit 117. The line of sight sensor 111 is configured to detect obstacles in front of the user. The main body assembly 107 is secured to a front portion of the user. A navigation module 115 is in the main body assembly 107 and is configured to locate the user and report navigation information to the central processing unit 117. A headset assembly 109 includes a line of sight sensor and a pair of headphones. The headset assembly 109 being worn in communication with a head of the user. The line of sight sensor of the headset assembly 109 tracks the viewing direction of the head in relation to the main body assembly 107. The central processing unit receives data communication from the line of sight sensors in the main body assembly and the headset assembly to detect the obstacles in the path of the user as determined by the navigation module. The central processing unit synthesizes the data communication and the navigation information to generate a 3D audible output to the user through the pair of headphones. The 3D audible output is a real time audible representation of the physical environment of the user. Additional features and functions are illustrated and discussed below.

Referring now to the Figures wherein like reference characters identify corresponding or similar elements in form and function throughout the several views. The following Figures describe embodiments of the present application and its associated features. With reference now to the Figures, embodiments of the present application are herein described. It should be noted that the articles "a", "an", and "the", as used in this specification, include plural referents unless the content clearly dictates otherwise.

As stated previously, system 101 includes main body assembly 107 and a headset assembly 109. Assembly 107 is worn by the user, typically around the waist or in communication with the torso of the user. It is preferred that assembly 107 be securely connected to the user to aid the sensors in operation. If assembly 107 is coupled to only a piece of clothing, it is highly likely to move and shift during movements of limbs of the user or in the wind. The position of main body assembly 107 should be secured relative to the user. Additionally, it is desired that it is not obstructed in view by clothing or other items.

Assembly 107 includes a LOS sensor 111, a camera assembly 113, a navigation module 115, and a central processing unit 117. Obstacle avoidance technology 103 includes the use of LOS sensor 111 and camera assembly 113 for the detection of obstacles, static and/or dynamic. LOS sensor 111 is configured to track and detect obstacles in front of the user. Sensor 111 can monitor a 180 degree field of view in front of the user. Unit 117 is configured to receive data communication regarding detected obstacles and assigns a 3D audio marker to each. The direction and location are represented through the headphones. Sensor 111 tracks objects in the peripheral vision of the user and is not reliant on the visual orientation of the user to identify and then subsequently notify the user of the obstacle. The line of sight of the user is useful in pinpointing the precise location of the obstacle proprioceptively by turning of the head independent of the walking or facing direction of assembly 107. The peripheral detected obstacles are automatically adjusted in distance and location in the headphones in relation to the line of sight of the user. In other words, the 3D audio output is aligned and adjusted in accordance with the line of sight of headset assembly 109. This works both vertically and horizontally.

A power module 119 is included to provide power to the components within system 101. This is ideally done through the use of a power supply or stored charge (i.e. battery). Camera assembly 113 is configured to collect video data of the user's surroundings or environment and transmit the video data to unit 117 for processing. The video data may be used to assist in identifying and locating obstacles. Furthermore, the video data may be used to capture one or more characteristics of the obstacle, such as size, color, text recognition on a sign and so forth.

A portable electronic device 121 is included and is in communication with at least one of the main body assembly 107 and the headset assembly 109. Device 121 includes an input/output interface for receiving inputs from the user. An example of device 121 would be a portable cellular phone with a touch screen. Application software can be downloaded onto device 121 for operation of and regulation of one or more system performance characteristics. An example of a system performance characteristic could include the sound level, navigation settings, location settings, and general system parameters, such as gaze focusing, radius adjustments, and focus settings.

The function of gaze focusing allows the user to adjust the peripheral vision of the user's audible environment. For example, the user may be focused on a particular area and is uninterested in peripheral events. Therefore, the user can decrease the sound level of peripheral markers to minimize distraction. This can apply in space both horizontally and vertically and are realized in the adjustment of sound levels assigned to obstacles.

The function of radius adjustment allows the user to adjust the distance of vision of system 101. This permits the user to either mute or minimize the emphasis (i.e. sound level) of objects beyond the selected radius. The radius may be increased, if for example the user was in a park or wide open space. Alternatively the radius may be decreased if the user was in a confined space.

The function of focus settings are similar to those of radius adjustment and gaze focus. Focus settings are settings particular to a type of environment and situation. These can be automatically applied when detected or can be manually adjusted. For example, system 101 may detect that the user is running and therefore automatically adjust radius, gaze focus, and navigation settings to accommodate.

System 101 may further include a manual user interface 123 in communication with the central processing unit 117 and the headset assembly 109. The manual user interface 123 is a link between the user and the central processing unit 117 such that activation of the manual user interface can adjust system performance characteristics. Interface 123 may be a roller ball, button, or switch, for example, that when manually activated, a function within system 101 is performed.

A conceivable, although not limiting, use of device 121 and interface 123 is that ability of the user to instantaneously capture, assign, or classify objects or information within the 3D audio environment. For example, with a click/single activation of interface 123 the user can send input data to unit 117 to assign a classification to an object in the line of sight of headset assembly 109. This method of operation is also applicable to permit the user to selectively store at least one of points of interest and landmarks for the user. Interface 123 can be configured to permit various selectable functions through a plurality of sequential activations. For example, a single activation performs a first task. A double activation (push button twice) performs a secondary task and so forth.

It is understood that system 101 may use either or both of interface 123 and device 121. Additionally, the functions and features of interface 123 may be combined into the functions and features of device 121.

Navigation module 115 is configured regulate and facilitate the functions of navigation technology 105 and can include everything necessary to report navigation information to unit 117, such as GPS, navigation software applications, online capable through cellular networks and WiFi, voice command systems, waypoint calculator, warning calculator, and landmark calculator for example. Module 115 can receive navigation information from the user. This can include a destination to be navigated to, points of interest or landmarks, a selection of maps (indoor/outdoor) to use for navigation purposes and so forth. The navigation information is transmitted to unit 117 for processing. Other functions of module 115 is the ability to automatically memorize routes taken by the user so as to provide the user the ability to retrace the route temporarily without having to reset a location destination. Additionally, module 115 can store details associated with commonly taken routes of the user. For example, points of interest to the user may be stored for recall at later times, like a restaurant.

Unit 117 is configured to receive the navigation information, input data, and data communication to generate the 3D audio output to the user. The sounds produced are assigned a specific distance and direction within the audible environment. Other functionality of unit 117 is realized. Unit 117 is also configured to store and identify the location of repeatedly encountered obstacles along a route. For example, if a user takes the same route to work and there is a pot hole in the road that the user has to navigate around, module 115 can store that pot hole as an obstacle in the route during future travels. These stored details are stored in terms of at least its location and may also be stored in terms of identification.

Furthermore, unit 117 can utilize constant bearing decreasing range logic to detect objects on a collision course with the user. Additionally, unit 117 is configured to automatically regulate system performance characteristics as a result of the environment of the user.

Figure 4:
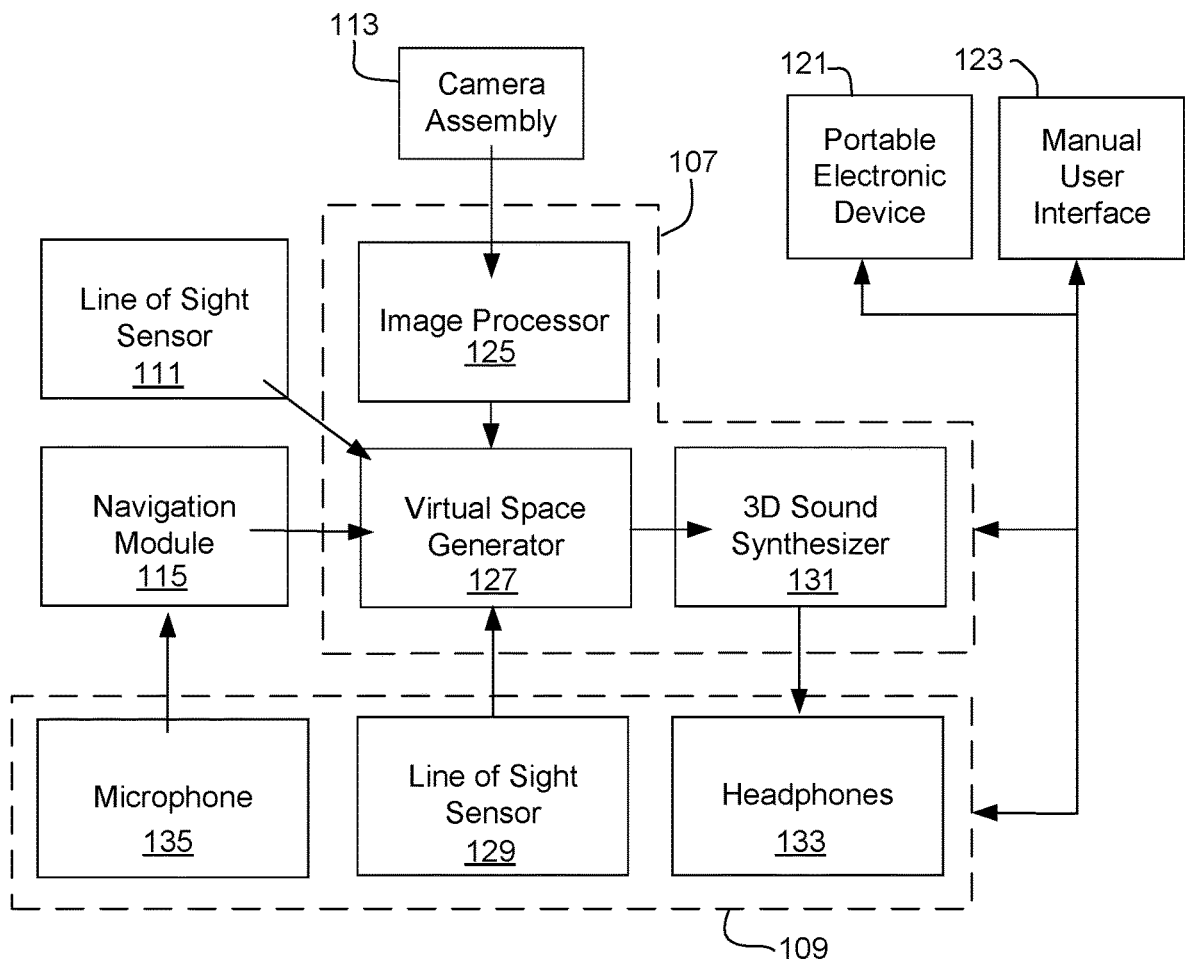
FIG. 4 is a detailed diagram of the route guidance and obstacle avoidance system of FIG. 3.

Referring now also to FIG. 4 in the drawings, a more detailed diagram of system 101 is illustrated. In FIG. 4, portions of unit 117 are isolated to visually see its interaction with other components in system 101. Unit 117 includes an image processor 124, a virtual space generator 127 and 3D sound synthesizer 131. Camera assembly 113 transmits video data to an image processor 125 within unit 117. The image processor 125 then communicates with a virtual space generator 127.

Generator 127 receives data from the image processor 125, sensor 111, module 115, and a LOS sensor 129 in assembly 109. The data is processed by generator 127 to calculate the relative pointing direction of assembly 109 with respect to assembly 107. A 3D virtual space is generated and oriented with respect to the orientation of assembly 109 line of sight. The line of sight is measured in azimuth and elevation. Different components may be used to assist in the functions of generator 127, such as a digital compass and digital tilt sensor to eliminate IMU drift and to reduce the need for calibration between sensors 111 and 129. In another embodiment the azimuth and elevation may be measured by an inertial measurement unit. Other components and methods are conceivable.

The data from generator 127 is passed to synthesizer 131 which is used to generate the 3D audio output. Synthesizer 131 applies 3D audio markers to objects, 3D audio beacons to navigational waypoints, linguistic tags to landmarks, and audio warning signs to warnings in the virtual space. This output is transmitted to headphones 133 in assembly 109. Sensor 129 is used to monitor the user's line of sight within the environment. Microphone 135 is used to transmit audible command data from the user to unit 117 through module 115.

Figure 5:
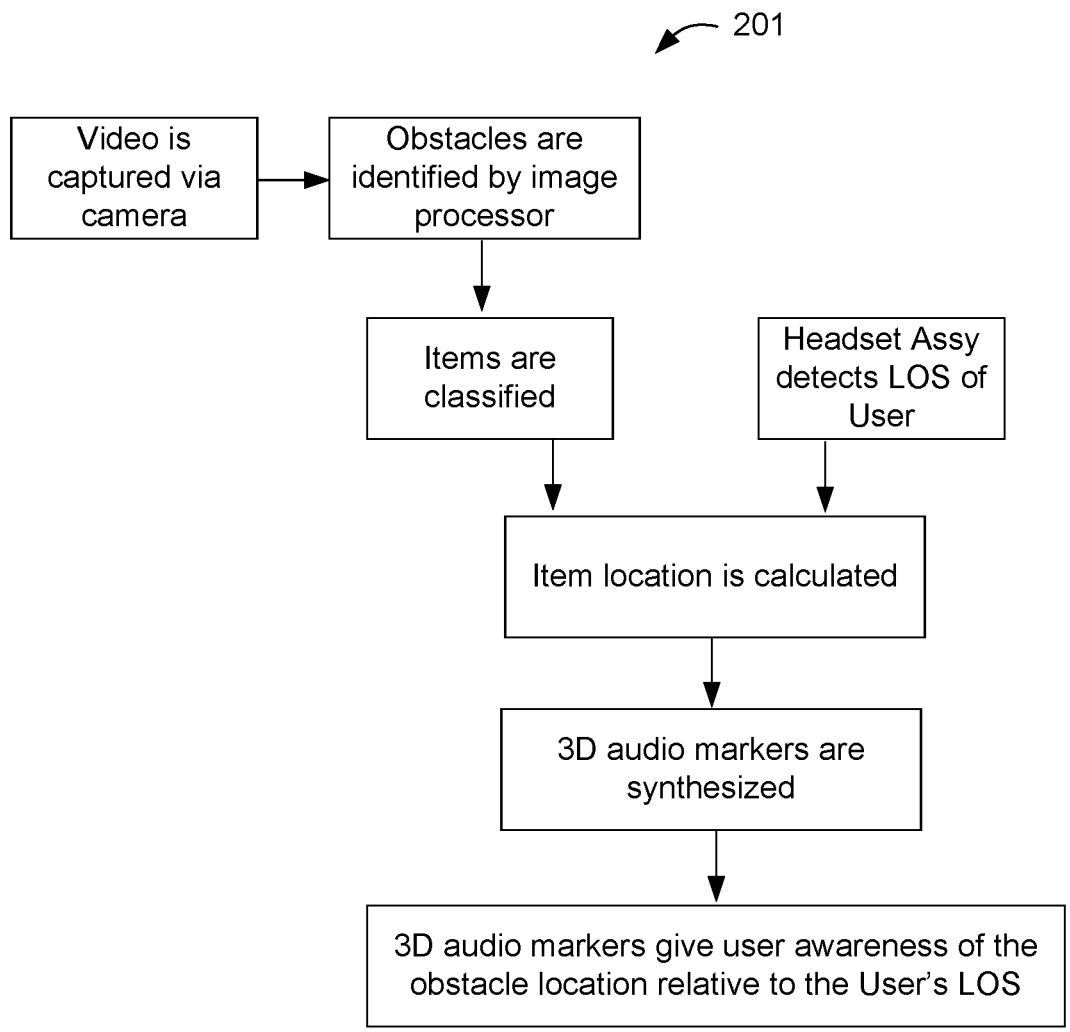
FIG. 5 is a diagram of a process of obstacle avoidance in the route guidance and obstacle avoidance system of FIG. 3.

Referring now also to FIG. 5 in the drawings, a diagram 201 of a process of identifying obstacles is provided. Video is captured through camera assembly 113 and sent to image processor 125. The images are processed to identify obstacles or pathways. These obstacles and pathways are then classified and the location of such item is calculated relative to the user's line of sight. Simultaneously, sensor 129 sends line of sight data for calculation and processing. The 3D audio markers are processed in synthesizer 131 and given a particular tone and location. These markers are adjusted in relation to the user's line of sight.

Figure 6:
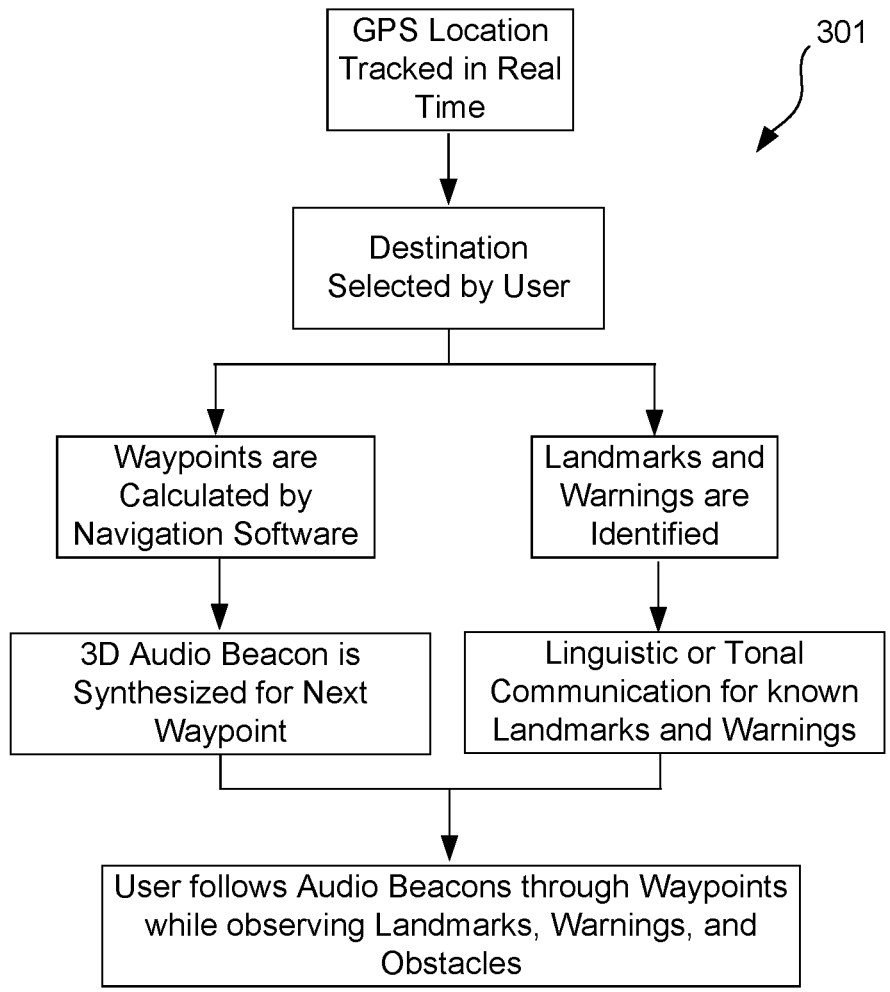
FIG. 6 is a diagram of a process of providing navigation in the route guidance and obstacle avoidance system of FIG. 3.

Referring now also to FIG. 6 in the drawings, a diagram 301 of a process of providing navigation is illustrated. The location of the user is tracked/monitored by system 101. The user may enter a location to travel to. System 101 then calculates waypoints via navigation software followed by the synthesizing of 3D audio beacons for the next waypoint. Concurrently, landmarks and warnings are identified and then linguistic or tonal communication for known landmarks and warnings are assigned. The user follows the audio beacons through the waypoints while observing landmarks, warnings, and obstacles. Obstacle avoidance is ongoing in conjunction with navigation.

It is evident by the foregoing description that the subject application has significant benefits and advantages over the prior art. Additional benefits are the ability of the user to record audio tags to locations or things. The tag may be assigned audibly or through device 121 or interface 123. It is then stored for recall at a later date. Such tags can be public or private. A user can tag the pot hole mentioned above and record that for future warning. Additionally, these tags may be sharable with others through a social network.

Possible applications for such technology as seen in system 101 is applicable in other markets. For example, in the military, soldiers receive use audio tags to increase situational awareness. Audio tags can represent locations of friends and foes, targets and rendezvous points, and other items of importance. Audio navigational beacons can be used by sighted people as well. For example, a user may ask to locate the library on a college campus or locate a store within an outdoor mall atmosphere. Audio tours can be enhanced through the introduction of augmented reality at places of interest like museums and historical sites. Another example is with a walkie talkie that adds direction to the person the other end of the line. This could assist in finding people in crowds, help a QB communicate with receivers, or assist emergency personnel find people.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

What is claimed is:

1. A route guidance and obstacle avoidance system for a visually impaired user, comprising:
   a main body assembly including a line of sight sensor and a central processing unit, the line of sight sensor configured to detect obstacles in front of the user, the main body assembly being secured to a front portion of the user;
   a navigation module in the main body assembly configured to locate the user and report navigation information to the central processing unit, the navigation module used to calculate waypoints for a selected destination; and
   a headset assembly including a line of sight sensor and a pair of headphones, the headset assembly being worn in communication with a head of the user, the line of sight sensor of the headset assembly being used to track the viewing direction of the head in relation to the main body assembly, the line of sight being measured in azimuth and elevation;
   a virtual space generator configured to receive data communication from the line of sight sensors, video data, and the navigation information from the navigation module to calculate a virtual 3D space relative to an orientation of the headset assembly and line of sight of the user, at least one of a digital compass and digital tilt sensor used with the virtual space generator to alleviate IMU drift with the virtual space generator;
   a synthesizer configured to receive data from the virtual space generator, the synthesizer configured to generate a 3D audio output including 3D audio markers for objects selectively located at particular locations within the virtual 3D space, the synthesizer generating a 3D audible output to the user through the pair of headphones, the 3D audible output being a real time audible representation of a physical environment of the user;
   wherein the synthesizer generates a 2D audio beacon for next waypoints along a route to the selected destination, the 3D audio beacon being located within the 3D audio output and used to navigate the user in the 3D audio environment.

2. The system of claim 1, further comprising:
   a camera assembly configured to collect the video data of the user's surroundings and transmit the video data to the central processing unit.

3. The system of claim 2, wherein the video data is used to classify an identify of the obstacle.

4. The system of claim 2, wherein the video data is used to capture one or more characteristics of the obstacle.

5. The system of claim 1, further comprising:
a portable electronic device in communication with at least one of the main body assembly and the headset assembly, the portable electronic device configured to receive user inputs from an input/output interface and transmit input data to regulate one or more system performance characteristics.

6. The system of claim 5, wherein the system performance characteristics relate to at least one of sound level through the pair of headphones, navigation settings, location setting, and general system parameters.

7. The system of claim 5, wherein the central processing unit is configured to receive the input data from the input/output interface to selectively store at least one of points of interest and landmarks for the user.

8. The system of claim 1, further comprising:
a manual user interface in communication with the central processing unit and the headset assembly, the manual user interface is a link between the user and the central processing unit such that activation of the manual user interface adjusts system performance characteristics.

9. The system of claim 8, wherein the system performance characteristics relate to at least one of sound level through the pair of headphones, navigation settings, location setting, and general system parameters.

10. The system of claim 8, wherein the central processing unit and headset assembly are configured to receive input data from the manual user interface to selectively store at least one of points of interest and landmarks for the user.

11. The system of claim 1, wherein the navigation module is configured to automatically memorize routes taken by the user so as to provide the user the ability to retrace the route temporarily without having to reset a location destination.

12. The system of claim 1, wherein the navigation module is configured to store details associated with commonly taken routes of the user.

13. The system of claim 1, wherein the central processing unit is configured to identify and automatically store the location of repeatedly encountered obstacles along the route.

14. The system of claim 1, wherein the central processing unit is configured to utilize constant bearing decreasing range logic to detect objects on a collision course with the user.

15. The system of claim 1, wherein the central processing unit regulates system performance characteristics.

16. The system of claim 1, wherein the central processing unit assigns a specific distance and direction to each sound.

17. A route guidance and obstacle avoidance system for a visually impaired user, comprising:
a main body assembly including a line of sight sensor and a central processing unit, the line of sight sensor configured to detect obstacles in front of the user, the main body assembly being secured to a front portion of the user;
a navigation module in the main body assembly configured to locate the user and report navigation information to the central processing unit, the navigation module used to calculate waypoints for a selected destination;
a camera assembly within the main body assembly configured to collect video data of the user's surroundings and transmit the video data to the central processing unit;
a headset assembly including a line of sight sensor and a pair of headphones, the headset assembly being worn in communication with a head of the user, the line of sight sensor of the headset assembly being used to track the viewing direction of the head in relation to the main body assembly, the line of sight being measured in azimuth and elevation;
a portable electronic device in communication with at least one of the main body assembly and the headset assembly, the portable electronic device configured to receive user inputs from an input/output interface and transmit input data to regulate one or more system performance characteristics;
a virtual space generator configured to receive data communication from the line of sight sensors, the video data, and the navigation information from the navigation module to calculate a virtual 3D space relative to an orientation of the headset assembly and line of sight of the user, at least one of a digital compass and digital tilt sensor used with the virtual space generator to alleviate IMU drift with the virtual space generator; and
a synthesizer configured to receive data from the virtual space generator, the synthesizer configured to generate a 3D audio output including 3D audio markers for objects selectively located at particular locations within the virtual 3D space, the synthesizer generating a 3D audible output to the user through the pair of headphones, the 3D audible output being a real time audible representation of a physical environment of the user;
wherein the synthesizer generates a 2D audio beacon for next waypoints along a route to the selected destination, the 3D audio beacon being located within the 3D audio output and used to navigate the user in the 3D audio environment.

18. The system of claim 17, wherein the navigation module is configured to automatically memorize routes taken by the user so as to provide the user the ability to retrace the route temporarily without having to reset a location destination.

19. The system of claim 17, wherein the central processing unit is configured to identify and automatically store the location of repeatedly encountered obstacles along the route.

20. The system of claim 17, wherein the central processing unit is configured to utilize constant bearing decreasing range logic to detect objects on a collision course with the user.

* * * * *